United States Patent
Mueller et al.

(10) Patent No.: US 11,564,618 B2
(45) Date of Patent: Jan. 31, 2023

(54) METHOD AND DEVICE FOR DETERMINING A DEGREE OF THERMAL DAMAGE TO HAIR

(71) Applicant: Henkel AG & Co. KGaA, Duesseldorf (DE)

(72) Inventors: Burkhard Mueller, Duesseldorf (DE); Torsten Lechner, Langenfeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 310 days.

(21) Appl. No.: 16/641,553

(22) PCT Filed: Aug. 13, 2018

(86) PCT No.: PCT/EP2018/071928
§ 371 (c)(1),
(2) Date: Feb. 24, 2020

(87) PCT Pub. No.: WO2019/048189
PCT Pub. Date: Mar. 14, 2019

(65) Prior Publication Data
US 2020/0221996 A1    Jul. 16, 2020

(30) Foreign Application Priority Data
Sep. 8, 2017    (DE) .................... 10 2017 215 873.5

(51) Int. Cl.
*A61B 5/00*    (2006.01)
*G01N 21/27*    (2006.01)
(Continued)

(52) U.S. Cl.
CPC .............. *A61B 5/448* (2013.01); *A45D 44/00* (2013.01); *G01N 21/274* (2013.01); *G01N 21/88* (2013.01);
(Continued)

(58) Field of Classification Search
CPC .... A61B 5/448; A61B 5/0075; G01N 21/274; G01N 21/33; G01N 21/47; G01N 21/64;
(Continued)

(56) References Cited

U.S. PATENT DOCUMENTS

2002/0006906 A1    1/2002   Stoltz et al.
2006/0281994 A1*  12/2006   Miyamae ........... G01N 21/3563
                                                          600/473
(Continued)

FOREIGN PATENT DOCUMENTS

CN    102198053 A   *   9/2011
DE    19506677 A1       8/1996
(Continued)

OTHER PUBLICATIONS

English Machine translation of CN 102198053 (Year: 2011).*
(Continued)

*Primary Examiner* — Dominic J Bologna
(74) *Attorney, Agent, or Firm* — Lorenz & Kopf, LLP

(57) ABSTRACT

A method and a device for determining a degree of thermal hair damage are provided. A method for determining a degree of thermal hair damage includes, during exposure of a hair sample of hair to UV or UV/VIS light, recording a spectrum of at least a portion of the UV or UV/VIS light that has interacted with the hair sample. Further, the method includes comparing at least a portion of the spectrum with a spectroscopic calibration model obtained using UV or UV/VIS spectra and degrees of thermal damage of a plurality of calibration hair samples. Also, the method includes determining the degree of thermal hair damage by using the comparison.

10 Claims, 1 Drawing Sheet

(51) Int. Cl.
*A45D 44/00* (2006.01)
*G01N 21/88* (2006.01)
*G01N 21/33* (2006.01)
*G01N 21/47* (2006.01)
*G01N 21/64* (2006.01)

(52) U.S. Cl.
CPC ...... *A45D 44/005* (2013.01); *A45D 2044/007* (2013.01); *A61B 5/0075* (2013.01); *G01N 21/33* (2013.01); *G01N 21/47* (2013.01); *G01N 21/64* (2013.01); *G01N 2201/12753* (2013.01)

(58) Field of Classification Search
CPC ......... G01N 2201/12753; G01N 21/88; A45D 44/005; A45D 2044/007; A45D 44/00
See application file for complete search history.

(56) References Cited

U.S. PATENT DOCUMENTS

| | | | |
|---|---|---|---|
| 2007/0100555 A1* | 5/2007 | Ladjevardi | G16H 20/70 356/402 |
| 2013/0222787 A1 | 8/2013 | Kajiki et al. | |
| 2015/0082553 A1* | 3/2015 | Landa | G01J 3/502 8/406 |
| 2017/0119130 A1 | 5/2017 | Witchell et al. | |
| 2019/0350515 A1 | 11/2019 | Mueller et al. | |

FOREIGN PATENT DOCUMENTS

| | | |
|---|---|---|
| DE | 60119210 T2 | 2/2007 |
| DE | 102016225674 A1 | 7/2017 |
| EP | 1629775 A1 | 3/2006 |
| JP | H0170161 U | 5/1989 |
| JP | H09173301 A | 7/1997 |
| JP | 2003240773 A | 8/2003 |
| JP | 2005283336 A | 10/2005 |
| JP | 2012242151 A | 12/2012 |
| JP | 2013200299 A | 10/2013 |
| JP | 2014522500 A | 9/2014 |
| WO | 2011024160 A1 | 3/2011 |
| WO | 2012174182 A1 | 12/2012 |
| WO | 2016/125164 A2 | 8/2016 |

OTHER PUBLICATIONS

EPO International Search Report issued in International Application No. PCT/EP2018/071928, dated Oct. 22, 2018.
McMullen et al.: "Thermal degradation of hair. I. Effect of curling irons", Journal of Cosmetic Science, Jul. 1998, vol. 49, pp. 223-244, XP055154260.
Tate et al.: "Quantification and prevention of hair damage", Journal of the Society of Cosmetic Chemists, vol. 44, 1993, pp. 347-371, XP055513866.
McMullen et al.: "Tryptophan fluorescence in hair-Examination of contributing factors", Journal of Cosmetic Science, Jan. 2011, pp. 291-304, XP055511932.
Cao et al.: "A novel method for non-destructive determination of hair photo-induced damage based on multispectral imaging technology", Scientific Reports, vol. 7, No. 1, Mar. 2017, XP055512249.
McMullen et al.: "Spectrofluorescent Characterization of Changes in Hair Chemistry Induced by Environmental Stresses", Journal of Cosmetic Science, Mar. 2011, vol. 62, pp. 191-202, XP055896607.

* cited by examiner

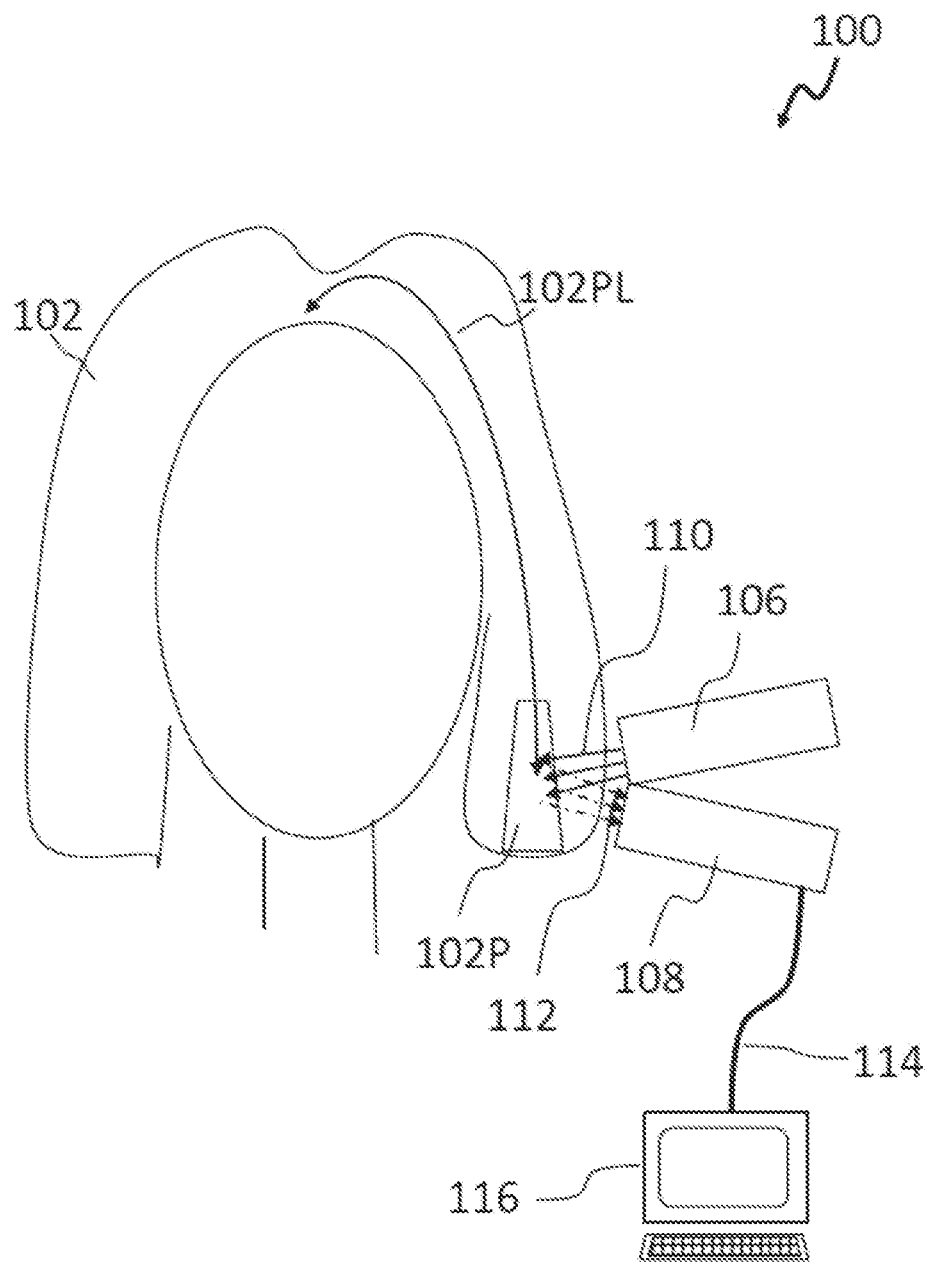

METHOD AND DEVICE FOR DETERMINING A DEGREE OF THERMAL DAMAGE TO HAIR

CROSS-REFERENCE TO RELATED APPLICATION

This application is a U.S. National-Stage entry under 35 U.S.C. § 371 based on International Application No. PCT/EP2018/071928, filed Aug. 13, 2018, which was published under PCT Article 21(2) and which claims priority to German Application No. 10 2017 215 873.5, filed Sep. 8, 2017, which are all hereby incorporated in their entirety by reference.

TECHNICAL FIELD

The present disclosure concerns a method and a device for determining a degree of thermal damage to hair and a method for determining a user-specific product for hair treatment.

BACKGROUND

When hair is treated with cosmetic products, an effect of the product, e.g. an intensity of a coloring, may depend strongly on the degree of damage to the hair.

Therefore, a determination of damage to the hair may be of great importance.

Hair may be damaged by natural or man-made processes. An important type of damage may be thermal damage.

When drying damp hair with a hairdryer, but especially during semi-permanent hair styling with a straightening iron or curling tongs, high temperatures (up to about 240° C.) act on the hair. Previously damaged hair, in particular, may be severely (further) damaged by such high temperatures.

The damaging process may be caused by a decomposition of amino acids, e.g. a decomposition of the amino acid tryptophan and its oxidation products (kynurenines) which are frequently found in hair.

In addition to chemical damage to the hair, physical damage may also occur, for example in the form of cracks in the hair cuticula.

These structural and chemical damages of the hair may lead to brittle hair, increased hair breakage during combing and an increase in combing work.

In the academic and industrial sector, a researcher or developer has a variety of physical and chemical analytical methods at his or her disposal to determine the degree of thermal damage, for example, a quantitative determination of the degree of thermal damage.

Chromatographic methods such as High-Performance Liquid Chromatography (HPLC) may be used to determine the content of an amino acid. However, these initially require a complex acidic, basic or enzymatic hydrolytic digestion of the hair sample. Alternatively, colorimetric methods may be used.

However, all of these methods are complicated and expensive, so that they are not available to the end user.

Damaging cosmetic treatments, such as hair coloration, heat treatments, perms or oxidative procedures such as bleaching, and many others, are typically performed in the private sector or in the field of commercial services to the end consumer. Although performing another damaging method on (thermally) previously damaged hair may lead to catastrophic results or even complete hair breakage, it has not been possible to determine the degree of previous thermal damage to the hair, for example quantitatively.

In addition, more and more users of products want a product tailored to their individual needs. This is especially true for cosmetic products such as skin and/or hair treatment products.

BRIEF SUMMARY

A method and a device for determining a degree of thermal hair damage are provided. A method for determining a degree of thermal hair damage includes, during exposure of a hair sample of hair to UV or UV/VIS light, recording a spectrum of at least a portion of the UV or UV/VIS light that has interacted with the hair sample. Further, the method includes comparing at least a portion of the spectrum with a spectroscopic calibration model obtained using UV or UV/VIS spectra and degrees of thermal damage of a plurality of calibration hair samples. Also, the method includes determining the degree of thermal hair damage by using the comparison.

In another embodiment, a device for determining a degree of thermal hair damage includes a UV light source or a UV/VIS light source for exposing a hair sample of the hair to UV or UV/VIS light. Further, the device includes a spectrometer for recording a spectrum of at least a portion of the UV or UV/VIS light that has interacted with the hair sample. Also, the device includes a data processing device having a data memory in which a spectroscopic calibration model obtained by means of UV or UV/VIS spectra and degrees of thermal hair damage of a plurality of calibration hair samples is stored, and having a processor for comparing at least a part of the spectrum with the spectroscopic calibration model and for determining the degree of thermal hair damage by using the comparison.

In various exemplary embodiments, a method and a corresponding device are provided which are easy to use and which enable a precise determination of a degree of thermal damage to hair by employing UV spectroscopy or UV/VIS spectroscopy.

In various exemplary embodiments, a mobile data processing device, e.g. a smartphone, a tablet or a laptop, may be used as device and method in a simple experimental procedure by using novel miniaturized UV sensors or UV/VIS sensors.

Furthermore, a method for the determination of individual hair treatment instructions is provided in various exemplary embodiments, which allows an end user to easily determine the degree of thermal damage, for example via the content of an amino acid, in his hair and to obtain a hair treatment instruction tailored to this purpose.

A UV spectrum or a UV/VIS spectrum may be obtained in various exemplary embodiments. The UV spectrum or UV/VIS spectrum may be an absorption spectrum or a fluorescence spectrum, for example.

For example, thermal hair damage may be determined in the form of a decrease in the tryptophan and/or kynurenine content by the decrease in the absorption band at about 280 nm in an absorption spectrum characteristic of tryptophan and kynurenines.

By applying mathematical models, a mathematical model may be created by measuring calibration hair samples, which have a degree of thermal damage determined by an alternative method, which then allows a calculation of a degree of thermal damage, for example a content of tryptophan and/or kynurenines, and thus of hair damage, in a hair sample, also called braid, of the consumer based on the recorded UV or UV/VIS spectrum. An analysis of the spectrum and an application of the model may be carried out with a smartphone, tablet, smart mirror or similar (with suitable apps).

In various exemplary embodiments, a method is provided to determine a degree of thermal hair damage. The method may comprise during exposure of a hair sample of the hair to UV or UV/VIS light, recording a spectrum of at least a portion of the UV or UV/VIS light that interacted with the hair sample, comparing at least a portion of the spectrum with a spectroscopic calibration model obtained by employing UV or UV/VIS spectra and degrees of thermal hair damage of a plurality of calibration hair samples, and determining the degree of thermal hair damage by using the comparison.

This method allows a direct, non-destructive determination of a degree of thermal hair damage, for example by determining the content of tryptophan and/or other components in a hair sample, without time-consuming sample preparation.

This method allows a faster achievement of results. Furthermore, it may be possible to subject the hairs to further treatments after the measurement, so that multiple applications may be performed on one strand of hair.

Furthermore, it may be possible to carry out relatively easy measurements at different hair positions (e.g. scalp-near and scalp-distant hair), for example directly on the head, without having to take the hair sample.

Ultraviolet radiation (UV radiation), colloquially often referred to as ultraviolet light (UV light), is electromagnetic radiation in a wavelength range from about 10 to about 380 nm. Within this wavelength range, a distinction is made between "near UV" (UV-A) with a wavelength range of from about 315 to about 380 nm, "medium UV" (UV-B) with a wavelength range of from about 280 to about 315 nm, "far UV" (UV-C-FUV) with a wavelength range of from about 200 to about 280 nm, "vacuum UV" (UV-C-VUV) with a wavelength range of from about 100 to about 200 nm and "extreme UV" (EUV) with a wavelength range of from about 10 to about 121 nm.

In the electromagnetic spectrum, the visible light (VIS) range comprises wavelengths from about 380 nm to about 780 nm.

In various exemplary embodiments, the UV light or UV/VIS light to which the hair sample is exposed may have a wavelength range of from about 200 to about 500 nm, especially preferably a wavelength range of from about 250 to about 400 nm and very preferably from about 250 to about 350 nm. In particular, it may be preferred that the UV light or UV/VIS light to which the hair sample is exposed has a wavelength range around about 280 nm, preferably between about 270 and about 290 nm.

In various exemplary embodiments, the method may further comprise the preparation of a calibration model, wherein the preparation of the calibration model may comprise: for the plurality of calibration hair samples, recording a calibration spectrum of at least a portion of the UV or UV/VIS light interacting with the calibration hair sample during exposure of the calibration hair sample to UV or UV/VIS light, determining a degree of thermal hair damage of the calibration hair sample by an independent method, and assigning the degree of thermal hair damage to the calibration spectrum, and determining a correlation between the plurality of calibration spectra and the plurality of thermal damage degrees.

In various exemplary embodiments, the independent method for determining a degree of thermal hair damage may involve determining a tryptophan and/or kynurenine content. The independent method may be a chromatographic or colorimetric method. The independent method may preferably be a chromatographic method for determining the tryptophan content.

In these exemplary embodiments, it may be advantageous that the interaction includes absorption of UV or UV/VIS light. It may be particularly preferred that the UV light or UV/VIS light to which the hair sample and/or calibration hair sample is exposed has a wavelength range around about 280 nm and that at least part of the UV or UV/VIS light has a wavelength range around about 280 nm.

Alternatively, the interaction may comprise reflection, scattering, transmission and/or fluorescence.

In various exemplary embodiments, the method may further include the creation of the calibration model, wherein the creation of the calibration model may comprise: for the plurality of calibration hair samples, obtaining a spectrum of at least a portion of the UV or UV/VIS light interacting with the calibration hair sample during exposure of the calibration hair sample to UV or UV/VIS light, determining an intensity ratio of the intensity of UV or UV/VIS light to which the calibration hair samples were exposed to the intensity of UV or UV/VIS light detected in the spectrum for each detected wavelength, determining a degree of thermal hair damage of the calibration hair sample by an independent method, and assigning the degree of thermal hair damage to the calibration ratio, and determining a correlation between the plurality of calibration ratios and the plurality of degrees of thermal damage.

In various exemplary embodiments, the independent method for determining a degree of thermal hair damage may comprise determining a fictitious period of hair damage.

In these exemplary embodiments, calibration hair samples are exposed to a temperature higher than about 180° C., preferably about 200° C., in a time series test for a certain period of time, for example from 0 to about 240 minutes. In defined time intervals, the calibration hair samples are irradiated with UV light or UV/VIS light. At least a part of the UV or UV/VIS light that has interacted with the calibration hair samples is detected. The ratio of the intensity of the irradiated UV or UV/VIS light to the intensity of the detected UV or UV/VIS light is then determined for each detected wavelength. This results in an intensity ratio of irradiated UV or UV/VIS light to reflected and/or emitted and/or transmitted and/or scattered UV or VIS light that is characteristic of the respective degree of thermal damage.

In various exemplary embodiments, at least a part of the UV or UV/VIS light which has interacted with the hair sample and/or the calibration hair sample may have a wavelength range from about 200 to about 600 nm, more preferably from about 300 to about 400 nm and very particularly preferably from about 300 to about 350 nm.

In various exemplary embodiments, a device is provided to determine the degree of thermal hair damage. The device may comprise a UV light source or UV/VIS light source for exposing a hair sample of the hair to UV or UV/VIS light, a spectrometer for recording at least a part of a spectrum of UV or UV/VIS light which has interacted with the hair sample, and a data processing device with a data memory, in which a spectroscopic calibration model obtained by employing a plurality of calibration hair samples is stored, and including a processor for comparing at least a part of the spectrum with the spectroscopic calibration model and for determining the degree of thermal hair damage with reference to the comparison.

The UV light source may be, for example, the UV LED light module "FluoroVu" by Eigen Imaging Inc.

In various exemplary embodiments, the UV or UV/VIS light source and the spectrometer may form an integrated unit.

A suitable miniaturized UV/VIS spectrometer, which operates in a wavelength range from about 200 to about 850 nm, is available from Ocean Optics, Inc. under the designation USB2000+UV-VIS.

In various exemplary embodiments, the integrated unit and/or the data processing device may be mobile devices.

In various exemplary embodiments, the UV or UV/VIS light source and the spectrometer may be integrated in a, preferably mobile, data processing device, in particular a smartphone or a tablet. Alternatively, the UV or UV/VIS light source and the spectrometer may form an integrated unit which, for example by employing suitable connectors, may be physically connected to a, preferably mobile, data processing device.

In various exemplary embodiments, a method is provided for determining individual, i.e. user-specific, treatment instructions depending on the degree of thermal damage determined.

According to various embodiments, the individual treatment instructions may include the recommendation of bleaching products and/or hair dyes and/or hair care products and/or hair styling products. It is particularly preferred that the individual treatment instructions include the recommendation of hair care products and/or hair styling products.

The recommendation may include the display or announcement of a specific product name and/or product image of a bleaching product and/or hair dye and/or hair care product and/or hair styling product. Alternatively, the recommendation may comprise the display and/or announcement of a product line or series (name, text and/or image), in particular a bleaching product line/series and/or hair dye line/series and/or hair care product line/series and/or hair styling product line/series, of a manufacturer.

It is preferred that the recommended bleaching product and/or hair dye and/or hair care product and/or hair styling product contains ingredients which are matched to the degree of thermal damage to the hair determined. It is particularly preferred that the recommended bleaching product and/or hair dye and/or hair care product and/or hair styling product provides heat protection. Heat protection may be achieved, for example, by using film-forming polymers and/or polysiloxanes in the hair treatment products. Octyl acrylamide/acrylates/butyl amino ethyl methacrylate copolymer (INCI) in particular can be used as a film-forming polymer. Suitable polysiloxanes include in particular PEG-14 dimethicone (INCI).

It is therefore preferred that the recommended bleaching products and/or hair dyes and/or hair care products and/or hair styling products comprise an ingredient selected from the group including film-forming polymers, polysiloxanes and mixtures thereof.

In an alternative embodiment of the method, the individual treatment instructions comprise the recommendation to refrain from bleaching and/or oxidative dyeing and/or permanent deformation and/or heat treatments for a certain period of time. Such individual treatment instructions may be given in particular if the degree of thermal hair damage is relatively classified as "very severe" and/or "severe".

In a further, advantageous embodiment of the method, the individual treatment instructions include advising or advising against the use of hair treatment products that the user of the method and/or the individual identifies by employing QR codes, NFC chips, barcodes or RFID chips.

In this embodiment of the method, the user of the method, for example a hairdresser or any other person at the point of sale of hair treatment products, may determine suitable or unsuitable hair treatment products after determining the degree of thermal damage via QR codes, NFC chips, barcodes or RFID chips, which are attached to the hair treatment product itself or to the place where it is stored, for example on the shelf in the hairdresser's shop or at the point of sale of hair treatment products.

QR codes, NFC chips, barcodes or RFID chips enable information to be transmitted wirelessly.

A barcode is an optoelectronically readable font including parallel lines and spaces of different widths. The data in a barcode is read by machine using optical reading devices, such as barcode readers (scanners) or cameras, and processed electronically. Many smart terminals have software that allows the digital camera of the smart terminal to capture the data and immediately display the code information to the user in decoded form.

A QR code ("Quick Response") is a two-dimensional code including a square matrix of black and white squares that represent the encoded data in binary form. Smart terminals usually have a built-in camera. After photographing the QR code, software is used to read/interpret the QR code.

NFC chips and RFID chips are transmitter-receiver systems. In this case, at least one communication partner must be active, i.e. stimulate communication. The other partner may be a chip without power supply, for example. This passive part is also called transponder (=transmitter+responder). In addition to active-passive communication between, for example, a smart terminal as active communication partner and a transponder/chip, active-active communication is also possible.

Coupling/excitation is affected by alternating magnetic fields with a short range generated by the active communication partner or by high-frequency radio waves. This not only transfers data, but also supplies the transponder with energy. The active communication partner, for example a smart terminal, contains software that controls the actual reading process and so-called middleware with interfaces to other (mobile) data processing devices and/or databases.

RFID ("Radio Frequency Identification") works via radio waves. RFID technology comprises a very wide range of different chips and readers, which differ mainly in terms of storage capacity, manufacturing process, cost, frequency range and range.

NFC ("Near Field Communication") is a standardized specialization of RFID technology, which was developed especially for data transmission over short distances (max. about 10 cm).

QR codes, NFC chips, barcodes or RFID chips, for example, may contain information on the degree of thermal damage for which the corresponding hair treatment product is or is not suitable.

The method for determining individual treatment instructions may also include initiating an online ordering process of the determined hair treatment product (bleaching product and/or hair dye and/or hair care product and/or hair styling product) and/or providing an indication of where the determined hair treatment product (bleaching product and/or hair dye and/or hair care product and/or hair styling product) may be obtained.

In an alternative embodiment of the method, the individual treatment instructions include advising the user on the use of bleaching products and/or hair dyes and/or hair care products and/or hair styling products which are individually manufactured for the user and initiating an ordering process, preferably by calling up an Internet site of a manufacturer of individual bleaching products and/or individual hair dyes and/or individual hair care products and/or individual hair styling products.

More and more customers want a product individually tailored to their needs. This may be a product specially made for the customer or a so-called "mass-customized" product. In the case of a mass-customized product, individualization may be achieved by varying a few features of a product that are decisive from the customer's point of view. Preferably, these mass-customized products are based on the concept of modularization, which means that the product may be assembled individually from various modules/components.

There are often numerous interdependencies between the many different characteristics/ingredients of a product, which may be expressed as "commands" or "prohibitions". In order to obtain a clear product definition, it may be advantageous to use a product configurator for the ordering process. This configurator helps the customer to select the characteristics/ingredients and points out the permissible/non-permissible combinations of characteristics, whereby the latter may then not be selected.

In the case of bleaching products, hair dyes, hair care products and hair styling products, the relevant product characteristics include in particular the chemical ingredients of the products, the physical properties of the products and the type of packaging of the products. With the help of a product configurator, for example, the selection of chemically and/or physically incompatible ingredients or the selection of ingredients unsuitable for the determined degree of thermal hair damage may be avoided. Vice versa, the selection of suitable ingredients for the determined degree of thermal hair damage may be specified or suggested by the product configurator.

In various exemplary embodiments, a visit to a hairdresser may be recommended for certain degrees of thermal hair damage. In various exemplary embodiments, a booking process may be initiated directly via the software/app, which determines the degree of thermal damage. For this purpose, the contact data of hairdressers may be stored in the software/app and displayed to the user. In addition, the selection may be limited via filters, such as the postal code. Alternatively, the booking of a hairdresser appointment may be made via a separate software/app, such as Treatwell.

Accordingly, the individual treatment instructions may include the recommendation of a hairdresser appointment and the initiation of an appointment booking process.

It is also preferred that the individual treatment instructions are stored and used in subsequent methods for long-term recommendation.

In a further embodiment, before the individual treatment instructions are issued to the user, data reconciliation takes place between the (mobile) data processing device, especially a smartphone or tablet, and data stored in a cloud. This data may include, for example, data from users with the same or similar degrees of thermal hair damage as well as, if applicable, other identical or similar hair parameters and the recommendations/measures and empirical values derived therefrom with regard to a successful treatment. By updating the data in the cloud by taking up the experience of other users and including the data in the method for determining individual treatment instructions, optimal treatment instructions may always be determined for the user.

In various exemplary embodiments, information regarding a general health condition, nutritional habits and other behaviors of the user (e.g. daily outdoor/sun/water time, smoking habits, sports habits, etc.) may be used to determine the individual treatment instructions.

Determining the degree of thermal hair damage and/or determining the individual treatment instructions may be performed using an app/software on a tablet, laptop, smart mirror or smartphone. Accordingly, the app may be a "mobile app"(application software for mobile devices), a web app (application software according to the client-server model) or a desktop app (application software for a desktop computer).

In various exemplary embodiments, the software/app that determines the degree of thermal hair damage may be the same as that which determines the individual treatment instructions. In various exemplary embodiments, different software/applications may be used for some or all of the different procedures.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

Exemplary embodiments of the present disclosure are represented by a FIGURE and are explained in more detail below.

BRIEF DESCRIPTION OF THE DRAWINGS

It is understood that other embodiments may be used and structural or logical modifications may be made without deviating from the scope of protection of the present disclosure. It is understood that the features of the various exemplary embodiments described herein may be combined with each other unless specifically stated otherwise. The following detailed description is therefore not to be understood in a restrictive sense and the scope of protection of the present disclosure is defined by the appended claims.

FIG. 1 shows in view 100 a schematic representation of a method for determining a degree of thermal hair damage according to different exemplary embodiments.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

According to different exemplary embodiments, a hair sample 102P may be examined to determine the degree of thermal damage of a user's hair 102. The hair sample 102P may remain on the head or be removed. Hair sample 102P may be located at a distance 102PL from a user's scalp or may be removed from the user's scalp. The hair sample 102P may have a minimum amount of hair, which may be expressed as a minimum area that may be covered by the (e.g. flatly spread) hair sample 102P, for example at least about 1 cm$^2$, or as a minimum weight, for example at least about 0.5 g.

In various exemplary embodiments, a device may be used to determine the degree of thermal hair damage of the hair 102, as shown in FIG. 1, exemplarily schematically in view 100.

In various exemplary embodiments, the hair sample 102P may be spread out so that it covers at least one interaction area which is illuminated by a light source 106 with UV or UV/VIS light 110 and from which the light 110, after interaction with the hair sample 102 designated as light 112 to be analyzed, enters a spectrometer 108.

In various exemplary embodiments, the hair sample 102P may be illuminated with UV light 110 or UV/VIS light 110. UV light 110 may cover a wavelength range from about 200 to about 380 nm, or at least a suitable sub-range thereof, for example from about 250 to about 300 nm. UV/VIS light 110 may cover a wavelength range from about 200 to about 500 nm, or at least a suitable sub-range thereof, for example from about 250 to about 400 nm.

In various exemplary embodiments, a light source 106 of UV or UV/VIS light 110 may be, for example, a UV lamp or a UV/VIS lamp, or any other conventional light source providing a suitable light spectrum.

Thanks to progressive improvement of UV or UV/VIS spectroscopy devices, they may be provided in a miniaturized, e.g. mobile, form, for example as a unit which may have the light source 106 and the spectrometer 108 as integrated components.

In various exemplary embodiments, the spectrum may be transmitted to a data processing device 116. Data transmission is marked with the reference character 114. Transmission may be carried out in a known way, for example by employing a data cable (e.g. USB), wireless data transmission (e.g. Bluetooth, WLAN (Wi-Fi), Thread, ZigBee or Near Field Communication (NFC)), or a transmission may be carried out within a device if the spectrometer (and possibly the light source) is part of a data processing device (e.g. smartphone, tablet, laptop or smart mirror) or is removably attached to the data processing device (e.g. by employing a suitable connector) or, vice versa, the spectrometer 108 is designed with an integrated data processing device 116.

For receiving and processing the data and for modeling, the data processing device in various exemplary embodiments may be equipped with appropriate software, for example an app.

In various exemplary embodiments, the recorded UV or UV/VIS spectrum may be used in conjunction with the calibration model to determine the tryptophan content of the hair sample as described above.

In various exemplary embodiments, a fictitious damage period of the hair sample may be determined as described above using the recorded UV or UV/VIS spectrum in conjunction with the calibration model.

In various exemplary embodiments, the degree of thermal hair damage may be determined on a categorical scale (e.g. low, moderate, strong, very strong).

In various exemplary embodiments, the degree of thermal hair damage may be determined in a metric scale (e.g. a numerical value with arbitrary units, as a percentage of the tryptophan content or as a percentage of damage).

In various exemplary embodiments, the described method for determining a degree of thermal hair damage may be performed using a data processing device 116.

The data processing device may, as described above in connection with FIG. 1, include, for example, a mobile data processing device, such as a smartphone, tablet or laptop, but also any other computer, such as a smart mirror, or any other data processing device capable of storing and providing the data, performing the comparison and applying the model, and, if necessary, also creating the model, such as any data processing device with a sufficiently large data memory and a sufficiently powerful processor.

In various exemplary embodiments, the data processing device may have at least one input device for inputting information into the data processing device, for example for inputting tryptophan content measured values for calibration and, if necessary, for inputting instructions, parameters, user data, etc. for executing the method.

In various exemplary embodiments, the at least one input device may include a touch-sensitive screen, microphone and/or keyboard.

In various exemplary embodiments, the data processing device may include at least one output device for outputting information, for example for outputting results of the method.

In various exemplary embodiments, the at least one output device may include a (touch-sensitive) screen, loudspeaker and/or a printer.

In particular in a case where the degree of thermal hair damage is determined for a plurality of hair areas (for example at the base, middle and/or tips), the provision of the degree of thermal hair damage to the user may include a graphical representation, e.g. a display, e.g. using a display device as an output device (e.g. a (touch-sensitive) screen of a smartphone, tablet or smart mirror). In the graphical representation, the determined degree of thermal hair damage of the plurality of areas with a coding based on the degree of thermal hair damage may be displayed in a representation of the user (e.g. a schematic representation or on a photo of the user). For example, in a schematic representation of the user's hairstyle, areas of different degrees of thermal hair damage may be displayed with different colors and/or patterns, e.g. areas with a low degree of thermal hair damage green and areas with a high degree of thermal hair damage red, or similar. In another example, a photo of the user, e.g. a digital photo showing the user's hair or hairstyle, may be overlaid with different patterns, e.g. a dot pattern for areas of a high degree of thermal hair damage and a line pattern for areas of a low degree of thermal hair damage, or similar. Alternatively, the real-time display of the hair on/in a smart mirror may be used to show the determined thermal hair damage levels.

When graphically displaying the degree of thermal hair damage of at least one hair area, e.g. the majority of hair areas, the degree of thermal hair damage may be displayed in various exemplary embodiments only for the area(s) for which the degree(s) of thermal hair damage was/were determined. In various exemplary embodiments, an area for which a degree of thermal hair damage is displayed may be extrapolated beyond the hair area for which the degree of thermal hair damage has been determined, for example by taking into account typical damage distribution patterns.

In addition or alternatively, a display device may be used as an output device to present concrete treatment instructions to the user as images and/or text messages. For example, images of specific products may be displayed that are tailored to the user's degree of thermal damage.

In various exemplary embodiments, the at least one output device may include a loudspeaker and/or the at least one input device may include a loudspeaker. The input of information and/or voice commands is affected via the voice of the user. In this case the device has a module for voice recognition, preferably an intelligent personal assistant (voice assistant), such as Alexa by Amazon, Google Assistant by Google, Cortana by Microsoft or Siri by Apple.

In various exemplary embodiments, any program (e.g. an app) that provides such functionality may be used for modeling.

Exemplary Embodiment 1

1. Spectroscopic Calibration Model ("Fictitious Hair Damage Period")

To determine a spectroscopic calibration model, strands of hair of a certain width, for example about 5 mm, are first exposed to heat of about 200° C. for 0 to about 120 minutes in a time series experiment. At intervals of about 10 minutes, each strand of hair is irradiated with UV light with a wavelength of from about 250 to about 300 nm. The light that has interacted with the hair strands is detected in a wavelength range from about 300 to about 350 nm. Then the ratio of irradiated to detected UV light is determined for the range of from about 300 to about 350 nm. This results in a ratio of irradiated UV light to reflected and/or emitted and/or transmitted and/or scattered UV light that is characteristic of the respective degree of thermal damage. For each period of damage about 10 hair strands are measured and the values obtained are averaged using the Wilcoxon Signed-Rank Test.

2. Determination of the Degree of Thermal Hair Damage

To determine individual hair damage, at least one strand of hair, comprising about 100 hairs, of an individual is irradiated with UV light having a wavelength of from about 250 to about 300 nm, the light which has interacted with the hair strands is detected in a wavelength range of from about 300 to about 350 nm and the ratio of irradiated UV light to reflected and/or emitted and/or transmitted and/or scattered UV light is determined. Using the spectroscopic calibration model, a fictitious damage period at a temperature of about 200° C. is assigned to the obtained ratio. This may be carried out with an app/software on a tablet, laptop or smartphone, for example.

The fictitious hair damage periods are classified by the app/software into the following degrees of thermal hair damage:

| Fictitious hair damage periods at 200° C. | Degree of thermal hair damage |
|---|---|
| up to 10 minutes | low |
| 10 to 30 minutes | moderate |
| 30 to 60 minutes | strong |
| greater than 60 minutes | very strong |

According to the degree of thermal hair damage, the app/software determines a bleaching product recommendation and/or hair dye recommendation and/or hair care product recommendation and/or hair styling product recommendation.

Depending on the degree of thermal hair damage, the recommended bleaching products and/or hair dyes and/or hair care products and/or hair styling products should contain the following ingredients:

| Degree of thermal hair damage | Product recommendation |
|---|---|
| low | Product contains up to 0.5% by weight of polysiloxane, especially PEG-14 dimethicone (INCI) |
| moderate | Product contains up to 0.5% by weight of polysiloxane, especially PEG-14 dimethicone, and up to 0.5% by weight of film-forming polymer, especially octyl acrylamides/acrylates/butyl amino ethyl methacrylate copolymer (INCI) |
| strong | Product contains up to 1% by weight of polysiloxane, especially PEG-14 dimethicone, and up to 0.5% by weight of film-forming polymer, especially octyl acrylamide/acrylates/butyl amino ethyl methacrylate copolymer (INCI) |
| very strong | Product contains up to 2% by weight of polysiloxane, especially PEG-14 dimethicone, and up to 1% by weight of film-forming polymer, especially octyl acrylamide/acrylates/butyl amino ethyl methacrylate copolymer (INCI) |

Exemplary Embodiment 2

1. Spectroscopic Calibration Model ("Tryptophan Content")

To determine a spectroscopic calibration model, hair strands with different degrees of thermal hair damage (low, moderate, strong and very strong) are first irradiated with UV light with a wavelength of from about 270 to about 290 nm. The light that has interacted with the hair strands is detected in a wavelength range of from about 270 to about 290 nm. The ratio of irradiated to detected UV light is then determined for this range. In this way, a characteristic UV absorption spectrum for the respective degree of thermal hair damage is obtained. The spectra obtained for each degree of thermal hair damage are averaged.

Ten hair strands of each degree of thermal damage are then examined after basic chemical digestion by High-Performance Liquid Chromatography (HPLC) and the content of tryptophan is determined. The values obtained for each degree of thermal hair damage are averaged.

The tryptophan content averaged for each degree of thermal hair damage is assigned the corresponding averaged absorption spectrum.

2. Determination of the Degree of Thermal Hair Damage

To determine individual thermal hair damage, at least one strand of hair, comprising about 100 hairs, of an individual is irradiated with UV light with a wavelength of from about 270 to about 290 nm and the light which has interacted with the hair strands is detected in a wavelength range of from about 270 to about 290 nm. Using the spectroscopic calibration model, tryptophan content is assigned to the absorption spectrum obtained. This may be carried out with an app/software on a tablet, laptop or smartphone, for example.

According to the tryptophan content the app/software determines a bleaching product recommendation and/or hair dye recommendation and/or hair care product recommendation and/or hair styling product recommendation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodi-

The invention claimed is:

1. A method for determining a degree of thermal hair damage, comprising:
   during exposure of a hair sample of hair to UV or UV/VIS light, recording a spectrum of at least a portion of the UV or UV/VIS light that has interacted with the hair sample;
   comparing at least a portion of the spectrum with a spectroscopic calibration model obtained using UV or UV/VIS spectra and degrees of thermal damage of a plurality of calibration hair samples; and
   determining the degree of thermal hair damage by using the comparison, wherein the spectroscopic calibration model is obtained by:
      for the plurality of calibration hair samples:
         exposing the calibration hair samples to a heat of a predetermined temperature for a predetermined time period;
         during exposure of the calibration to the heat for the predetermined time period, exposing the calibration hair samples to UV or UV/VIS light at a plurality of time intervals;
         during exposure of the calibration hair samples to the UV or UV/VIS light at each of the plurality of time intervals, acquiring a spectrum of at least a portion of the UV or UV/VIS light that interacted with the calibration hair sample;
         at each of the plurality of time intervals, determining an intensity ratio of the intensity of UV or UV/VIS light to which the calibration hair samples were exposed to the intensity of UV or UV/VIS light detected in the spectrum for each detected wavelength;
         determining a degree of thermal hair damage of the calibration hair samples by an independent method;
         assigning the degree of thermal hair damage to the calibration spectrum; and
         determining a correlation between the plurality of calibration ratios and the plurality of degrees of thermal hair damage.

2. The method according to claim 1, wherein the exposure of the hair sample and/or the calibration hair sample is carried out with UV or UV/VIS light with a wavelength range of from about 270 to about 290 nm.

3. The method according to claim 1, wherein the independent method comprises determining a notional hair damage period.

4. The method according to claim 3, wherein the at least one part of the UV or UV/VIS light has a wavelength range of from about 300 to about 350 nm.

5. The method according to claim 1, wherein the exposure of the hair sample and/or the calibration hair sample is performed with UV or UV/VIS light of a wavelength of from about 250 to about 300 nm.

6. A method for determining individual treatment instructions, comprising:
   determining a degree of thermal hair damage of an individual according to claim 1; and
   determining, via a computer-aided determination, individual treatment instructions depending on the degree of thermal hair damage.

7. The method according to claim 6, wherein the individual treatment instructions comprise the recommendation of bleaching products and/or hair dyes and/or hair care products and/or hair styling products.

8. A device for determining a degree of thermal hair damage, comprising:
   a UV light source or a UV/VIS light source for exposing a hair sample of the hair to UV or UV/VIS light;
   a spectrometer for recording a spectrum of at least a portion of the UV or UV/VIS light that has interacted with the hair sample; and
   a data processing device having a data memory in which a spectroscopic calibration model obtained by means of UV or UV/VIS spectra and degrees of thermal hair damage of a plurality of calibration hair samples is stored, and having a processor for comparing at least a part of the spectrum with the spectroscopic calibration model and for determining the degree of thermal hair damage by using the comparison,
   wherein the spectroscopic calibration model is obtained by:
      for the plurality of calibration hair samples:
         exposing the calibration hair samples to a heat of a predetermined temperature for a predetermined time period;
         during exposure of the calibration to the heat for the predetermined time period, exposing the calibration hair samples to UV or UV/VIS light at a plurality of time intervals;
         during exposure of the calibration hair samples to the UV or UV/VIS light at each of the plurality of time intervals, acquiring a spectrum of at least a portion of the UV or UV/VIS light that interacted with the calibration hair sample;
         at each of the plurality of time intervals, determining an intensity ratio of the intensity of UV or UV/VIS light to which the calibration hair samples were exposed to the intensity of UV or UV/VIS light detected in the spectrum for each detected wavelength;
         determining a degree of thermal hair damage of the calibration hair samples by an independent method;
         assigning the degree of thermal hair damage to the calibration spectrum; and
         determining a correlation between the plurality of calibration ratios and the plurality of degrees of thermal hair damage.

9. The device according to claim 8, wherein the UV or UV/VIS light source and the spectrometer form an integrated unit.

10. The device according to claim 8, wherein the integrated unit and/or the data processing device are mobile devices.

* * * * *